(12) United States Patent
Holl

(10) Patent No.: US 8,783,096 B2
(45) Date of Patent: Jul. 22, 2014

(54) HARDNESS TESTING DEVICE AND METHOD FOR ADJUSTING THE HARDNESS TESTING DEVICE

(75) Inventor: Robert Holl, Scheffau (AT)

(73) Assignee: Qness GmbH, Golling an der Salzach (AT)

( * ) Notice: Subject to any disclaimer, the term of this patent is extended or adjusted under 35 U.S.C. 154(b) by 205 days.

(21) Appl. No.: 13/397,821

(22) Filed: Feb. 16, 2012

(65) Prior Publication Data

US 2012/0210777 A1 Aug. 23, 2012

(30) Foreign Application Priority Data

Feb. 17, 2011 (AT) .................................. A 211/2011

(51) Int. Cl.
*G01N 3/48* (2006.01)
*G01N 3/42* (2006.01)
(52) U.S. Cl.
CPC .......... *G01N 3/42* (2013.01); *G01N 2203/0647* (2013.01); *G01N 2203/0078* (2013.01)
USPC ............................................................ 73/81
(58) Field of Classification Search
USPC ........................................... 73/78, 81, 82, 85
See application file for complete search history.

(56) References Cited

U.S. PATENT DOCUMENTS

| 3,106,093 | A | * | 10/1963 | Walker et al. ..................... 73/81 |
|---|---|---|---|---|
| 4,304,123 | A | | 12/1981 | Aschinger et al. |
| 4,611,487 | A | | 9/1986 | Krenn et al. |
| 5,355,721 | A | | 10/1994 | Las Navas Garcia |
| 5,616,857 | A | * | 4/1997 | Merck et al. ...................... 73/82 |
| 6,247,356 | B1 | * | 6/2001 | Merck et al. ...................... 73/82 |
| 6,301,956 | B1 | | 10/2001 | Fujita et al. |
| 2003/0196480 | A1 | * | 10/2003 | Anderberg ........................ 73/81 |
| 2005/0016264 | A1 | * | 1/2005 | Anthe et al. ..................... 73/82 |
| 2007/0199371 | A1 | * | 8/2007 | Ernst ................................. 73/81 |
| 2009/0145196 | A1 | * | 6/2009 | Kawazoe et al. ............. 73/1.89 |
| 2010/0122572 | A1 | * | 5/2010 | Scherzinger et al. ............. 73/81 |

FOREIGN PATENT DOCUMENTS

| DE | 3000984 A1 | 7/1980 |
|---|---|---|
| DE | 3506437 A1 | 9/1985 |
| DE | 19960017 A1 | 6/2000 |
| GB | 678527 A | 9/1952 |

OTHER PUBLICATIONS

Austrian Office Action, dated Feb. 15, 2012, from corresponding Austrian patent application No. A 211/2011.

* cited by examiner

*Primary Examiner* — Hezron E Williams
*Assistant Examiner* — Marrit Eyassu
(74) *Attorney, Agent, or Firm* — Young & Thompson

(57) ABSTRACT

A hardness testing device has at least one penetrator (9), arranged on a holder (15), for producing an impression (27) in an object under test (3) and at least one lens (12) for detecting at least one measure of the impression (27) in the object under test (3), which can be positioned alternately over the object under test (3). The holder (15) is mounted on the hardness testing device (6) in such a way as to be able to rotate around its longitudinal axis.

13 Claims, 5 Drawing Sheets

HARDNESS TESTING DEVICE AND METHOD FOR ADJUSTING THE HARDNESS TESTING DEVICE

The invention relates to a hardness testing device with at least one penetrator that is arranged on a holder for producing an impression in an object under test and at least one lens for detecting at least one measure of the impression in the object under test, which can be positioned alternately on the object under test.

In addition, the invention relates to a method for setting the rotating position of a hardness testing device penetrator that is mounted on a holder.

Hardness testing devices are known that have both penetrators and optical systems to be able to measure immediately the impression that is produced by the penetrator. The penetrator and the optical system, in particular the lens thereof, are in this case arranged on swivel elements or turrets so that, after the impression is produced, it can be measured directly by the penetrator by pivoting the swivel element or rotating the turret.

It often occurs that in an object under test, not only a single measurement but rather a measurement series is to be made, whereby the measurement series has to have a certain orientation to the object under test, for example at a right angle to a specific object edge. A penetrator that produces in particular a square or rhombic impression that deviates from a circular impression in general has in this case to have a certain orientation relative to this object edge.

In these cases, it is necessary to rotate the workpiece or the object under test to the extent that the position of the impression corresponds to a specified or necessary layer. This is not only time-consuming but also inaccurate when the orientation of the object under test is not done precisely.

The object of the invention is therefore to make available a hardness testing device, in which this expense or these inaccuracies are avoided.

This object is achieved in a hardness testing device of the above-mentioned type in such a way that the holder is mounted on the hardness testing device in such a way as to be able to rotate around its longitudinal axis.

In addition, this object is achieved in a method of the above-mentioned type in that the penetrator on the holder is rotated around the longitudinal axis thereof until the orientation of the penetrator corresponds to a target position.

In the invention, the method is employed not to rotate the object under test but rather to rotate the penetrator on its holder until the penetrator or the impression produced by the latter in the object under test corresponds to a specified orientation or target position, in which a precise measurement of at least one measure to the impression is possible. All impressions of this measurement series produced by penetrators are subsequently in the correct position, so that no further positioning of the object under test is necessary for an exact measurement.

When the penetrator on its holder is fastened in a defined or known position, and the holder in turn is positioned in a defined or known position on the hardness testing device, in particular the swivel element or turret, the orientation of the penetrator is known and can be either manually or preferably electronically controlled by the hardness testing device being rotated into the necessary position.

If, however, the rotating position of the penetrator on its holder is not known and/or the holder is arranged in an undefined rotating position on the hardness testing device, then the rotating position of the penetrator on the holder has to be determined or set, so that the latter can then be controlled manually or electronically in a simple way and can be rotated in the correct position relative to the object under test.

To set or to determine the rotating position of the penetrator on the hardness testing device, it is provided in a preferred embodiment of the invention that on the holder, a reference point is arranged to which a reference point that is arranged in a stationary manner on the hardness testing device is assigned.

In this embodiment of the invention, the penetrator is mounted on the hardness testing device by means of its holder in such a way that the two reference points have a defined position relative to one another, for example they lie exactly opposite one another. Subsequently, for example, the actual orientation or rotating position of the penetrator is then established by a sample impression, and a correction angle of rotation is determined by which the penetrator has to be rotated so that it occupies a certain position. This correction angle of rotation can then be added to an angle in which the penetrator for the actual measurement has to be oriented. This angle can be preset, for example, by a preset or defined position of the object under test during the measurement or can be determined before the measurement either by hand or automatically by the hardness testing device, or more precisely its optics in connection with software, which can detect and evaluate the position of the object under test recorded by the optics.

Theoretically, it is also possible, of course, to determine the position of the penetrator relative to its reference point on the holder and the correction angle of rotation produced therefrom outside of the hardness testing device, and then to take it into consideration accordingly during incorporation of the penetrator into the hardness testing device.

When the correction angle of rotation is automatically or electronically taken into consideration, the latter is stored in the control for a certain penetrator and automatically taken into consideration when a measurement is to be made with this penetrator. Since frequently entire measurement series are pre-programmed in electronically controlled hardness testing devices, a fully automatic measurement is also possible from the larger series with different objects under test after the correction angle of rotation is established for the first time without a manual adjustment or taking the position of the object under test into consideration relative to the rotating position of the penetrator being necessary.

By such a reference point, the exact positioning of the penetrator on the hardness testing device is always possible all over again, even when the penetrator was detached from the hardness testing device and is mounted again at a later time.

As an alternative to determining a correction angle of rotation, which has to be taken into consideration during any measurement, it is also possible according to the invention that the reference point on a carrier is arranged to move in the direction of rotation of the holder and is fastened in a fixable manner to the holder. In this embodiment of the invention, the correction angle of rotation can thus be taken into consideration on a one-time basis in such a way that the reference point on the holder is mounted on the holder rotated by this correction angle of rotation so that the reference points lie exactly opposite one another in the starting or basic position of the penetrator; subsequently, therefore, the correction angle of rotation no longer has to be taken into consideration or is zero.

Other preferred embodiments of the invention are subjects of the other subclaims.

Other features and advantages will emerge from the following description of preferred embodiments of the invention with reference to the attached drawings. Here:

Figure 1:
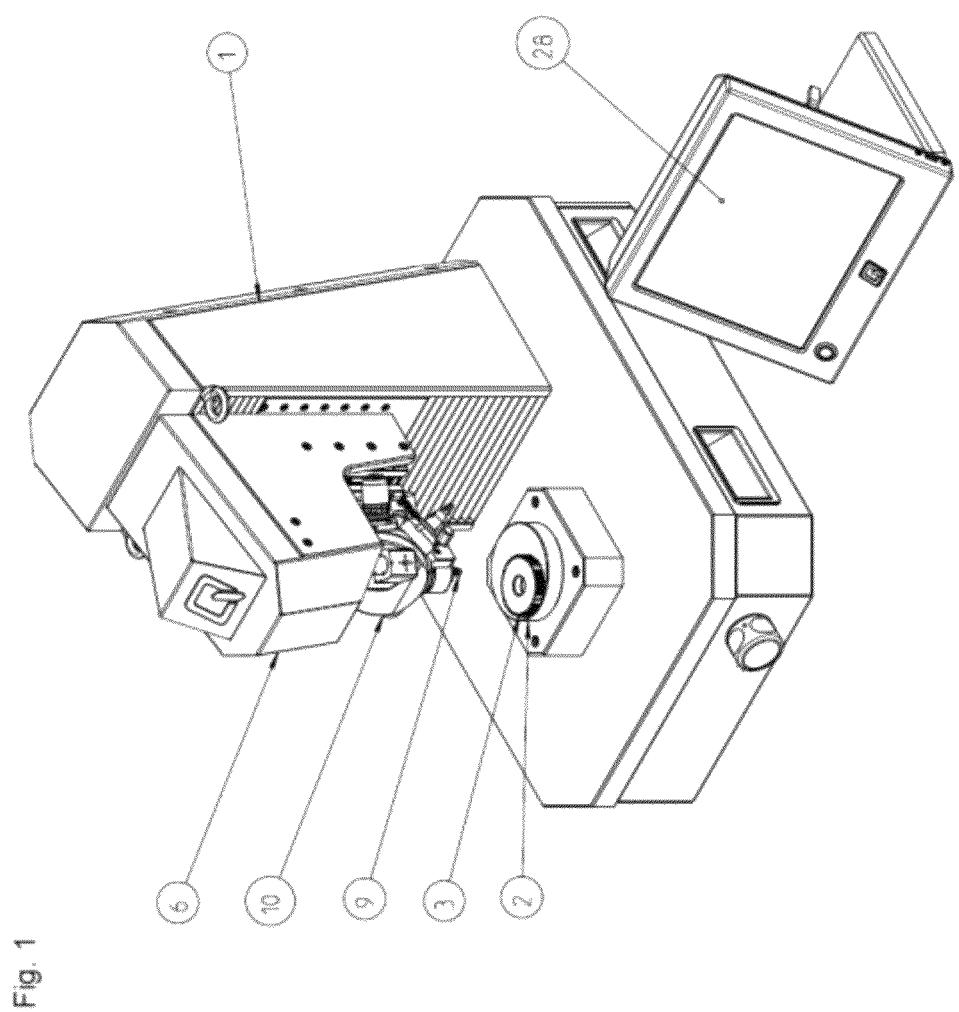
Figure 2:
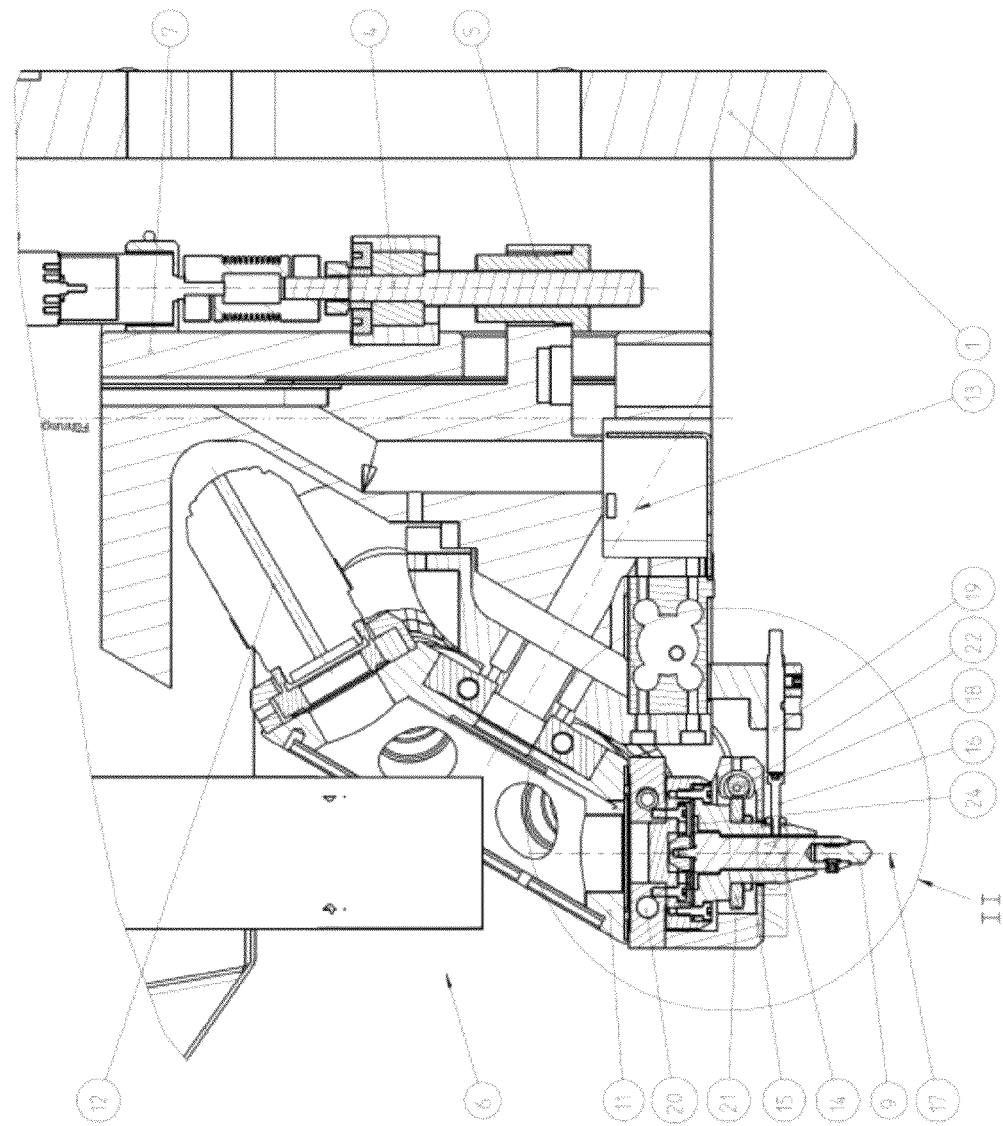
Figure 3:
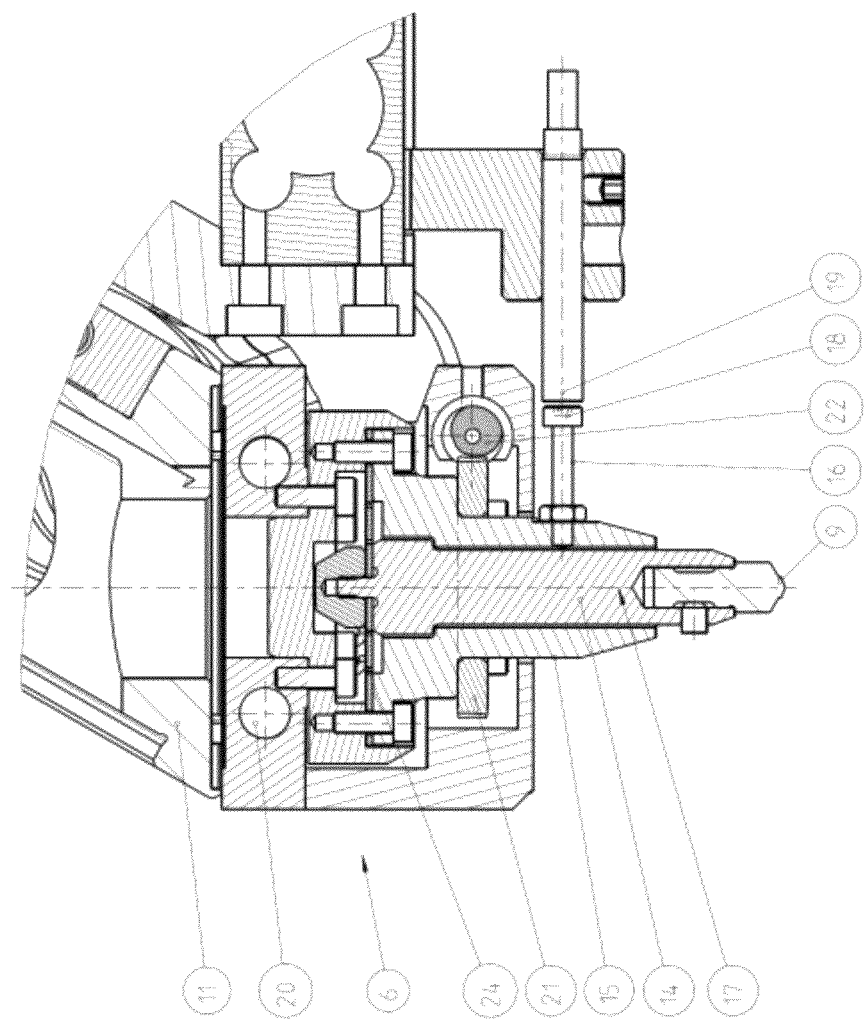
Figure 4:
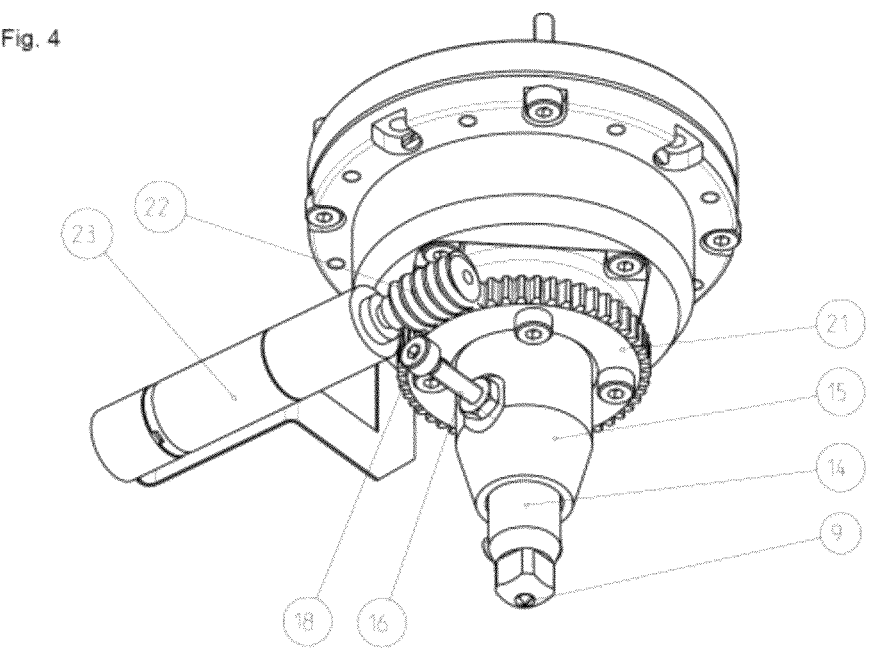
Figure 5:
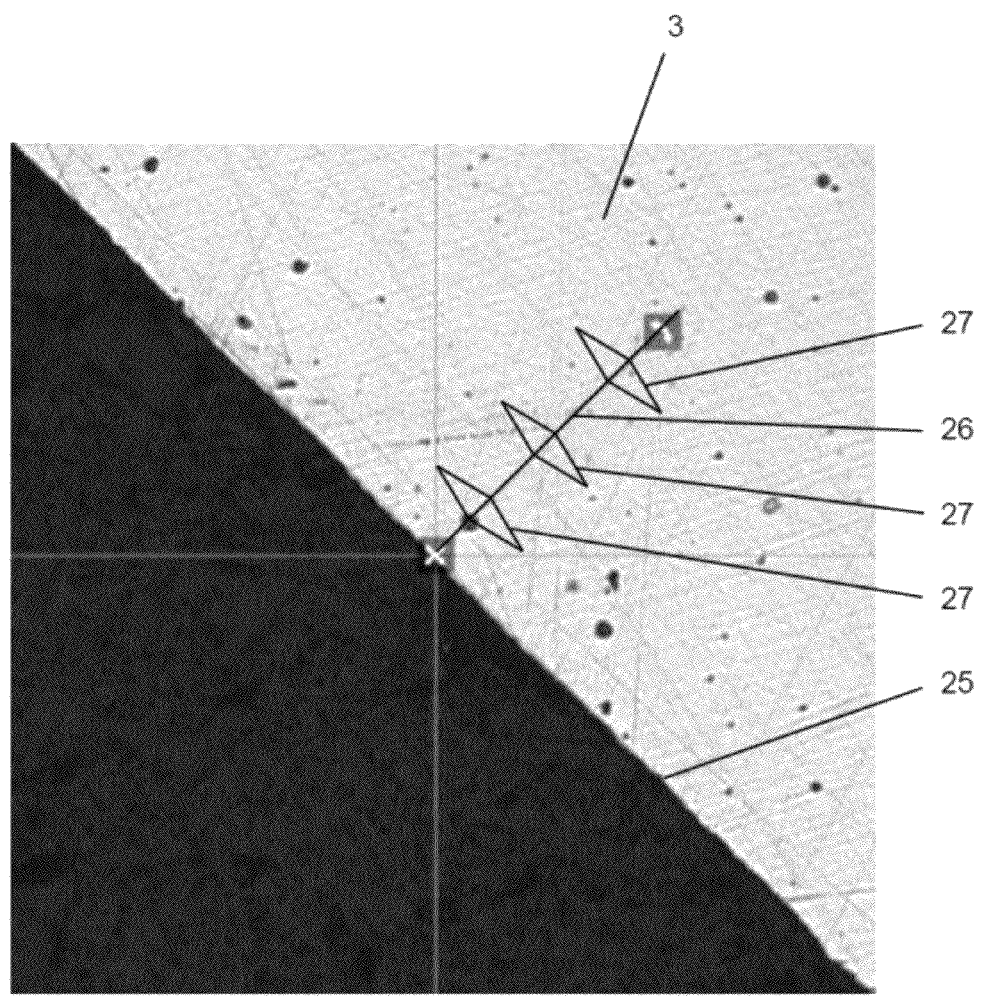

FIG. 1 shows an embodiment of a hardness testing machine with a hardness testing device in oblique view according to the invention, FIG. 2 shows a section through an embodiment of a hardness testing device, FIG. 3 shows an enlarged view of a detail of the hardness testing device of FIG. 2, FIG. 4 shows another detail of the hardness testing device of FIG. 2, and FIG. 5 shows a microscopic image of an object under test.

The hardness testing machine shown in FIG. 1 has a machine frame 1 with a table 2 on which objects under test 3, a pipe in the example that is shown, are placed. An electric motor, which drives a vertically oriented threaded spindle 4 over a spindle gear, is arranged under the table 2. A spindle nut 5 interacts with the threaded spindle 4, which is connected to a hardness testing device 6. In addition, the hardness testing device 6 can be moved back and forth on the machine frame 1 by a vertical guide 7, not shown in detail, i.e., toward and away from the object under test 3. In addition, a holding-down clamp can be arranged on the hardness testing device 6, which is used to clamp the object under test 3 on the machine table 2 to allow an exact measurement.

At least one penetrator 9, which can be, for example, a penetrator for a hardness testing according to Vickers, Brinell or Rockwell depending on the measurement method used, is arranged on the hardness testing device 6. The machine according to the invention is not limited to a specific form and type of hardness testing but rather can be used for all possible or known forms and types of hardness testing; however, it is preferably used in penetrators that produce, for example, square and in particular rhombic impressions that deviate from a circular impression.

In the embodiment according to FIG. 1, a test probe 10 is shown in the form of a swivel element, and in the embodiment according to FIGS. 2 and 3, a test probe 11 is shown in the form of a turret, on which penetrator 9 and lens 12 are located, which are oriented at an angle of 45° to the axis of rotation 13 of the test probe 11 and are rotated in their working position depending on the test method to be used. In the embodiment of FIGS. 2 and 3 shown, the penetrator 9 is in the working position.

The penetrator 9 is fastened to a carrier 14 that can move axially in a holder 15 but is not held in a rotatable manner. A carrier in the form of a pin 16, which has a reference point 18 on its free end, is mounted on the holder 15. The reference point 18 can be designed, for example, as a magnetic or magnetizable, for example, pin-shaped insert on the end of the pin 16. A reference point 19, which is fastened to the hardness testing device 6, is assigned to the reference point 18. The reference point 19 is designed, for example, as a sensor for the insert on the pin 16, which sensor detects when the reference point 18 lies exactly opposite it. Other detection systems, such as, e.g., an optical detection system, for example with a reflector as a reference point 18 and an optical transceiver, are also conceivable as a reference point 19.

The holder 15 is mounted in such a way as to be able to rotate via a roller bearing 20 on the turret 11 around the longitudinal axis 17 thereof. To rotate the holder 15, a gear 21 is fastened to the latter, so that it is rotated by means of a worm shaft 22. A motor 23, which is fastened to the hardness testing device 6, is provided for the drive of the worm shaft 22.

When the hardness testing device 6 is driven downward via the spindle drive 4, 5, i.e., is moved toward the object under test 3, while the penetrator 9 rests on the object under test 3, the carrier 14 moves upward within the holder 15 relative to the latter, by which the force can be measured with a force measuring system 24, with which the penetrator is pressed on the object under test 3.

When the exact rotating position of the penetrator 9 on its carrier 14 and/or the rotating position of the carrier 14 in the holder 15 and/or the rotating position of the holder 15 on the turret 11 is/are not known exactly, first a sample impression is made on an object under test to determine the exact rotating position of the penetrator 9, and the reference points 18, 19 in this sample impression lie exactly opposite. Based on the angle of rotation of the sample impression on the object under test relative to a reference position or reference line, a correction angle of rotation can then be determined and has to be rotated around the penetrator 9 on its holder 15 so that it occupies its basic position or reference position. Assuming that the penetrator 9 is rotated counterclockwise by 15° relative to its basic position or reference position, these 15° correction angles of rotation have to be taken into consideration in any further adjustment.

FIG. 5 shows a microscopic image of an object under test 3 with an object edge 25, in which, for example, three measurements with rhombic penetrators 9 that produce the rhombic impressions 27, shown in FIG. 5, are to be made along a line 26, which is oriented at an angle of 90° to the object edge 25.

If the object edge 25 is rotated counterclockwise, for example, at an angle of 45° to a vertical reference line or reference position, the penetrator 9, starting from the position in which the reference points 18, 19 lie exactly opposite to one another, has to be rotated counterclockwise in its target position only by an angle of 30°, when the correction angle of rotation is, for example, 15°, as assumed earlier.

Since the exact rotating position of the penetrator 9 or the correction angle of rotation is known, the latter can be input into the control unit of the hardness testing device 6, optionally stored there, and subsequently automatically taken into consideration when a measurement on an object under test 3 is to be made with a defined orientation or target position of the impressions produced by the penetrator 9. The position of the object under test 3 in this case either can already be predefined in the control unit in a large automated measurement or can be fed electronically into the control unit, or can be determined from case to case and be input into the control unit, whereby this can be done either semi-automatically by a computer-aided recognition system or manually.

FIG. 1 shows a monitor 28 of a control unit. Data relevant to the measurement, such as, e.g., the correction angle of rotation, can be input and output via the monitor, when the latter is designed as a touchscreen, or via a keyboard. Relevant data for the measurement can also be digitally input and output via suitable interfaces.

The invention claimed is:

1. Hardness testing device comprising:
   a test probe (11) rotatable about a first axis of rotation (13);
   a holder (15) on the test probe and being rotatable about a second axis of rotation (17) different from the first axis of rotation;
   at least one penetrator (9), on the holder (15), for producing an impression (27) in an object under test (3); and
   at least one lens (12), on the test probe, for detecting at least one measure of the impression (27) in the object under test (3),
   which wherein the holder and the at least one lens are positionable alternately over the object under test (3).

2. Hardness testing device according to claim 1, wherein the holder (15) comprises a reference indicator (18) and the hardness testing device (6) further comprises a stationary reference sensor (19) that detects the reference indicator.

3. Hardness testing device according to claim 2, further comprising a carrier (16) mounted on the holder, wherein the reference indicator (18) is fixed to the carrier (16) and wherein the carrier is arranged in the direction of rotation of the holder (15).

4. Hardness testing device according to claim 2, further comprising a carrier (16) mounted on the holder, wherein the reference indicator (18) is movably mounted on the carrier, and wherein the carrier is arranged in the direction of rotation of the holder.

5. Hardness testing device according to claim 2, further comprising a control unit, with a storage device, in which a set value is stored for an angle of rotation of the holder (15) for at least one holder (15) with a specific penetrator (9).

6. Hardness testing device according to claim 2, wherein the hardness testing device (6) has a power drive (23) for the holder (15).

7. Hardness testing device according to claim 1, wherein the hardness testing device (6) has a power drive (23) for the holder (15).

8. Hardness testing device according to claim 1, wherein the first and second axes of rotation are 45 degrees apart.

9. Method for setting a rotating position of a penetrator (9) of a hardness testing device (6) that is mounted on a holder (15), where the hardness testing device includes a test probe (11) rotatable about a first axis of rotation (13), where the holder is on the test probe and is rotatable about a second axis of rotation (17) different from the first axis of rotation, where the hardness testing device includes a lens on the test probe for detecting a measure of an impression make by the penetrator in an object under test, the method comprising:

rotating the test probe around the first axis of rotation so that the penetrator in the holder is over the object under test; and rotating the penetrator (9) on the holder (15) around the second axis of rotation (17) until the orientation of the penetrator (9) corresponds to a target position.

10. Method according to claim 9, wherein the rotation of the penetrator (9) is established relative to a reference position and wherein an established angle deviation is stored as a correction angle of rotation.

11. Method according to claim 10, wherein when the holder (15) is rotated to bring it into the target position, the correction angle of rotation is incorporated into the angle of rotation.

12. Method according to claim 10, further comprising bringing a first reference point that is fixed in the direction of rotation on the holder into a starting position relative to a second reference point that is arranged in a stationary manner on the hardness testing device, then rotating the holder is with the penetrator until the orientation of the penetrator corresponds to the reference position, and then storing the established angle deviation as the correction angle of rotation.

13. Method according to claim 10, further comprising bringing a first reference point on the holder into a starting position relative to a second reference point that is arranged in a stationary manner on the hardness testing device, then rotating the holder with the penetrator until the orientation of the penetrator corresponds to the reference position, and then fixing the first reference point on the holder by the established angle deviation rotated on the holder (15).

* * * * *